United States Patent [19]

Nandagiri et al.

[11] Patent Number: 5,554,363

[45] Date of Patent: Sep. 10, 1996

[54] METHOD OF REDUCING MALODORS IN PERMANENT WAVING

[75] Inventors: Arun Nandagiri, Libertyville; Bruce H. Solka, Chicago; John A. Kocis, Palatine, all of Ill.

[73] Assignee: Helene Curtis, Inc., Chicago, Ill.

[21] Appl. No.: 371,353

[22] Filed: Jan. 11, 1995

Related U.S. Application Data

[63] Continuation of Ser. No. 17,239, Feb. 12, 1993, abandoned.

[51] Int. Cl.⁶ ....................................................... A61K 7/09
[52] U.S. Cl. ........................ 424/70.51; 132/203; 424/70.2
[58] Field of Search ............................... 424/70.2, 70.51; 132/202, 203, 204, 205, 209

[56] References Cited

U.S. PATENT DOCUMENTS

| | | | |
|---|---|---|---|
| 4,547,365 | 10/1985 | Kubo et al. | 424/70.5 |
| 4,548,811 | 10/1985 | Kubo et al. | 424/70.51 |
| 4,560,554 | 12/1985 | Kubo et al. | 424/70.4 |
| 5,352,443 | 10/1994 | Kubo et al. | 424/70.2 |
| 5,419,895 | 5/1995 | Kubo et al. | 424/70.51 |

FOREIGN PATENT DOCUMENTS 3640748  2/1988  Germany.

*Primary Examiner*—Melvyn I. Marquis
*Assistant Examiner*—Robert H. Harrison
*Attorney, Agent, or Firm*—Marshall, O'Toole, Gerstein, Murray & Borun

[57] ABSTRACT

A method of treating hair to reduce post-perm odor by (1) reducing the degree of reaction between a permanent wave reducing agent and a natural compound contained in hair, e.g., hair aldehydes; and/or (2) altering the malodor of products formed by the reaction of hair and a permanent wave reducing agent, during the oxidation step; and/or (3) binding a fragrance to the hair to mask any odoriferous compounds that result from reaction of a reducing agent with the hair, or from the reaction of reduced hair with an oxidizing agent; and/or (4) change the naturally occurring post-perm odor by adding a reducing agent reactant during the permanent waving process resulting in more pleasant smelling reaction products.

9 Claims, No Drawings

METHOD OF REDUCING MALODORS IN PERMANENT WAVING

CROSS-REFERENCE TO RELATED APPLICATION

This is a CONTINUATION of U.S. application Ser. No. 08/017,239, filed Feb. 12, 1993, now abandoned.

FIELD OF THE INVENTION

The present invention is directed to a method of treating hair to reduce or alter an unpleasant post-perm odor associated with the contact of hair with a reducing agent or oxidizing agent in permanent waving of hair. More particularly, the present invention is directed to a method of lessening the amount of reaction of a reducing agent with compounds naturally present in hair that produce malodor, e.g., hair aldehydes, by reacting a portion of the permanent wave reducing agent, e.g., cysteamine, with a reactant other than an odor-producing hair reactant, e.g., hair aldehydes. In another embodiment, malodor is reduced by adding a reactant to the hair after rinsing the reducing agent and prior to oxidation to lessen malodor resulting from a reaction of a reducing agent reaction product and the oxidizing agent. The resulting reaction products formed by reaction of (1) the added reactant and (2) (a) the reducing agent; and/or (b) a malodorous reaction product of the oxidizing agent with the reduced hair, substantially lessens the objectionable odor otherwise identified with the permanent waving process, e.g., more pleasant smelling than the common reducing agent/hair aldehyde reaction product; or oxidizing agent/reduced hair reaction product, normally formed in the permanent waving process.

BACKGROUND OF THE INVENTION AND PRIOR ART

In general, permanent waving of human hair is achieved by chemically breaking the sulfur to sulfur or disulfide cystine bonds occurring naturally in human hair and then reforming the cystine bonds while the hair is wrapped or curled on rods. The sulfur to sulfur cystine bonds in human hair maintain the hair in a naturally straight or curly configuration. In order to permanently reshape the hair into a lasting, different configuration, a significant percentage of the sulfur to sulfur bonds must be broken and then reestablished after the hair is reconfigured in a desired position, such as wrapped around a suitable mandrel or roller. In general, the sulfur to sulfur cystine bonds are broken with a composition containing a reducing agent and after the hair is wound into a curl formation around a rod or roller, the sulfur to sulfur cystine bonds are relinked or reestablished while the hair is in the curl formation by contacting the hair in the new formation with an oxidizing agent, such as hydrogen peroxide or a water-soluble bromate.

It is well known in the art of hair permanent waving that conventional reducing agents used in permanent waves to alter hair configuration result in a characteristic unpleasant odor in the hair. The intensity and duration of this unpleasant odor is formula dependent, depending, in particular, on the reducing agent used in the waving process. Conventional waving agents that are widely used are Ammonium Thioglycolate, Glyceryl Monothioglycolate (GMT), Sodium or Ammonium Bisulfite, and Cysteamine. All of these reducing agents leave residual odor on the hair, after reaction with the hair, that lasts from a day to one or two weeks. Some of the factors that play a role in the amount of odor left in the hair include the concentration and type of reducing agent, and the pH of the waving lotion. Some of the reducing agents are inherently more odoriferous than others. For example, it is widely known that Cysteine Hydrochloride is less odoriferous than GMT and the odor of Sodium Bisulfite is different and sometimes less objectionable than the mercaptans (thioglycolates).

The thiol reducing agents, such as Ammonium Thioglycolate, Ammonium Dithioglycolate, Glyceryl Monothioglycolate, and the like, produce malodor due to the formation of disulphides as shown below

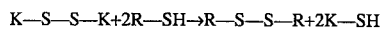

K—S—S—K+2R—SH→R—S—S—R+2K—SH

The reducing agent step of the permanent waving process forms cleaved disulfide (sulfide) hair sites, and other reaction products. The cleaved disulfide (cysteine) hair bonds having reactive sulfur sites are then oxidized, to reestablish the hair bonds in the new hair configuration. Oxidation of the hair sulfur bonds present after reducing agent contact results in reestablished disulfide hair bonds as well as other side reactions products that are odiferous. In accordance with one embodiment the present invention, a carbonyl-containing compound, e.g., aldehyde or ketone, is added to hair that has been reduced with a thiol reducing agent, after rinsing and before the oxidation step, to react a portion of the reduced hair with the carbonyl associated with the permanent waving process.

Post-perm odor has been cited by clients as one of the major drawbacks of permanent waving. Many attempts have been made by formulators to address this odor problem with only limited success. For example in a pending U.S. application, Ser. No. 07/919,972, filed Jul. 27, 1992, Kolc, Abbott, and Nandagiri, disclose a reducing agent composition including a combination of Ammonium Thioglycolate and Cysteine free base to reduce processing odor and post-perm odor while maintaining all other performance characteristics. In a Japanese patent application 3-271214 Segawa et al. disclose a post-penn treatment composition containing acids to reduce the odor of Cysteamine waved hair.

Major marketers of permanent wave products in the United States have attempted to minimize the odor problem by using fragrances in the reducing agent-containing wave lotion and/or in the oxidizing agent-containing neutralizing composition.

Although these approaches are being practiced in the art, they are all only partially effective in overcoming the problems of post-perm odor. While not being bound to any specific theory on the mechanism of action, it is theorized that one of the reasons why there is persistent post-perm odor is due to certain odoriferous residues formed by reaction of hair aldehydes with the reducing agent. It is theorized that these residues are left in the hair after the waving process as a result of being chemically bound to hair protein or as a result of the residues being trapped within the hair matrix. Malodor is given off from these residues when the hair is wetted. Over time, with repeated shampooing of the hair, these residues are released from the hair, leaving the hair pleasant smelling again.

Addressing this problem by simply fragrancing the hair, without chemical bonding of the fragrance to the hair, in an attempt to mask the unpleasant odor is not effective since the masking fragrance is not long-lasting and does not prevent or reduce the formation of the odoriferous reaction products. We have found that more effective ways of dealing with post perm odor are: (1) minimize or prevent the formation of these malodor residues; and/or (2) compete for the olfactory receptor sites within the nose, with compounds that chemically bind to the hair and are faster in reaching the receptor sites than the malodor residues; and/or (3) change the distribution of odiferous reaction products such that the perceived odor is less objectionable than the odor resulting from the distribution of naturally occurring reaction products that are otherwise formed with natural hair-containing reactants, such as hair aldehydes.

SUMMARY OF THE INVENTION

In brief, the present invention is directed to a method of treating hair to reduce post-perm odor by (1) reducing the degree of reaction between a permanent wave reducing agent and a natural compound contained in hair, e.g., hair aldehydes; and/or (2) altering the malodor of products formed by the reaction of hair and a permanent wave reducing agent, during the oxidation step; and/or (3) binding a fragrance to the hair to mask any odoriferous compounds that result from reaction of a reducing agent with the hair, or from the reaction of reduced hair with an oxidizing agent; and/or (4) change the naturally occurring post-perm odor by adding a reducing agent reactant during the permanent waving process resulting in more pleasant smelling reaction products.

It is, therefore, one aspect of the present invention to provide a more effective and more long-lasting solution to the problem of hair malodor resulting from permanent waving.

Another aspect of the present invention is to provide a composition which will prevent or minimize the formation of malodor residues in permanently waved hair.

Yet another aspect of the present invention is to chemically bind a pleasant smelling compound, in situ, in the hair which can effectively compete with malodor residues formed during permanent waving.

These and other aspects and advantages of the present invention will become more apparent from the following detailed description of the preferred embodiments.

DETAILED DESCRIPTION OF THE PREFERRED EMBODIMENTS

Post-perm odor associated with the use of a cysteamine reducing agent was studied in detail. It should be understood, however, that the present invention is applicable to reduction of post-perm odor resulting from the use of any reducing agent or oxidizing agent in the permanent waving of hair. Cysteamine is β-mercapto ethylamine having the formula:

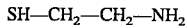

SH—CH$_2$—CH$_2$—NH$_2$

Hair permed with Cysteamine has a characteristic odor often described by clients as similar to the smell of popcorn or corn chips. Experiments were conducted in an attempt to isolate the odoriferous compound(s) formed during the permanent wave process that cause this distinctive odor. Comparisons of the chemical make-up of the hair before and after perming, using a cysteamine reducing agent, revealed that the major differences was the presence of post-perm "thiazolidine" type compounds that were absent in hair before perming.

Thiazolidines are formed by the reaction of Cysteamine with aldehydes in the hair by the following reaction:

SH—CH$_2$—CH$_2$—NH$_2$+RCHO→Thiazolidines and H$_2$O

Where R could be H, or C-1 through C-10, inclusive, e.g., any one or combination of the HCHO through C$_{10}$HO aldehydes, inclusive.

Thiazolidines are either chemically bound to hair protein or buried within the hair matrix or formed over time as one or both of the reactants (the reducing agent, e.g. cysteamine, or the reactive compound, e.g., aldehyde) becomes available to react. As a result, the malodor persists for a prolonged period of time and is not readily removed by shampooing the hair. The amount of thiazolidines formed varies with individuals, presumably due to the fact that the amount of aldehyde in the hair varies with each individual.

Evidence that these thiazolidines are odiferous is provided in U.S. Pat. No. 3,944,581 wherein the odors of about 65 synthesized thiazolidine derivatives are described. It has also been reported in the technical literature that cysteamine reacts readily with various aliphatic aldehydes and ketones. Ref: Yasuhara, A. and Shibamoto, T., "Determination of Volatile Aliphatic Aldehydes in the Headspace of Heated Food Oils by Derivatization with 2-aminoethanol", J. Chrom., 547 291–298 (1991). Japanese patent application 3-271214 discloses a post rinse composition to eliminate this odor; however, thiazolidines, once formed, cannot be broken down easily.

In accordance with the present invention, reducing post-perm odor is achieved by reacting one or more carbonyl-containing compounds, e.g., aldehydes or ketones, with the hair, or with reduced hair, to reduce, mask or alter the odor resulting from reactions of reducing agents with the hair, or resulting from oxidation of reduced hair. In accordance with one important embodiment of the present invention, hair is pre-treated with one or more reactive compounds that can chemically react with the reducing agent used in the permanent waving lotion to form, in situ (within the hair) compounds that are not odoriferous, or pleasantly odiferous. In order for this pretreatment to be effective, when the permanent waving process uses cysteamine as a reducing agent, it should have the following two properties:

(1) The pretreatment should reduce the amount of malodor thiazolidines that are formed by the reaction of (a) short, straight chain (C$_1$–C$_{10}$) aldehydes in the hair with (b) cysteamine; and (2) The pretreatment should have the chemical carbonyl group, e.g., aldehyde group or ketone group, necessary for reaction with the reducing agent to form non-odoriferous or more pleasant smelling compounds in the hair.

EXAMPLE 1

Hair swatches were treated with a permanent wave lotion containing cysteamine as the reducing agent. The thiazolidines formed were measured by GC Mass Spectroscopy. The hair sample was refluxed in water for 30 minutes. Organics in this reflux water were concentrated by solid phase extraction and then analyzed.

A separate set of swatches were pretreated with a composition containing Benzaldehyde, Methyl Hydrocinnamic Aldehyde, and a mixture of Benzaldehyde and Methyl Hydrocinnamic Aldehyde. This was followed by the same waving lotion, containing Cysteamine as the reducing agent. The thiazolidene content was measured in a similar manner by GC Mass Spectroscopy. Values obtained are shown in Table I below.

TABLE I

| | Concentrations (% by wt. of composition) | Total Thiazolidines parts per million of hair |
|---|---|---|
| No pretreatment | | 60/42 |
| Benzaldehyde Prewrap | 0.25% | 29 |
| Methyl Hydrocinnamic Aldehyde Prewrap | 0.7% | 35 |
| Benzaldehyde (0.25%) and Methyl Hydrocinnamic Aldehyde (0.7%) | 0.95% | 23 |

In addition to changing the total amounts of thiazolidines formed by reaction with the cysteamine reducing agent, evidence of the success of the approach is seen in the presence of thiazolidine derivatives after perming of the hair tresses. Exact identification of the individual products is uncertain because their electron impact mass spectra lack molecular ions. They do, however, exhibit the characteristic mass 88 fragment ion in relatively high abundance and are thus confidently identified as thiazolidine derivatives. After pretreatment with benzaldehyde and perming, with a fragrance including, among other components, triethyl acetophenone, hexylcinnamic aldehyde and other ketones and aldehydes, analysis of the unpermed hair reveals total free aldehydes in the $C_1$ to $C_{10}$ range in the low parts-per-million range. Thus, if the modifying, reactive compound is added to the hair in the 0.05% to 20% by weight range, based on the hair weight, the reactive compound will be present in amounts that are at least 50 times greater than the naturally occurring aldehydes. By this approach we "flood" the hair with the reactive compounds of our choice, resulting in a reducing agent-reactive compound reaction product having a better fragrance after perming.

EXAMPLE 2

An experiment was performed to determine if the reducing agent resulting in the lowest thiazolidene number would result in a permanent wave having less perm odor. Approximately 400 patrons were divided into two groups. Group one had their hair pretreated with aldehydes before perming. Group two had no pretreatment. Using a 1–5 scale, patrons in both groups were evaluated by an expert panel of four judges (blind) for post perm odor, one week after receiving permanent waves. Calibrated ratings of the four judges showed a significant reduction in odor in the groups that were pretreated with an aldehyde. In addition, patrons were also asked their opinion as to whether or not they perceived any post-perm odor. Results obtained are shown in Table II below.

TABLE II

| | First 200 Patrons | Second 200 Patrons |
|---|---|---|
| No Pretreatment | 22.0% | 12% |
| Pretreated with aldehydes | 16.0% | 7% |

For reduction of cysteamine reducing agent odor, a preferred pretreating composition is shown in Table III below.

TABLE III

| Ingredient | Wt. % |
|---|---|
| Water | 94.95 |
| Benzaldehyde | 0.25 |
| Fragrance 0/716530 (Dragoco Co.) (including 25% by weight methyl hydrocinnamic aldehyde; 17% by weight hexyl cinnamic aldehyde; 9% by weight cycloamine aldehyde and less than 0.1% by weight $C_{12}$ aldehydes) | 0.7 |
| PEG-15 Oleammonium Chloride (ETHOQUAD) (dispersing agent) | 0.2 |
| Sodium PCA (pyrrolidone carboxylic acid) (moisturizer) | 0.2 |
| Glycerine (moisturizer) | 0.2 |
| Octoxynol-13 (Igepal-730) (fragrance solubilizer) | 3.1 |
| Citric acid (50% active in water) (for pH adjustment) | 0.3 |
| Disodium ethylene diamine tetracetic acid (preservative) | 0.1 |

Any compound containing a carbonyl group (e.g., RCHO where $R=C_nH_{2n+1}$, or $R=C_nH_n$ where n=0 to 20, particularly the aromatic aldehydes, such as ring substituted benzaldehydes), will react with cysteamine to reduce post perm odor. Included in these carbonyl compounds are ketones and esters which react with cysteamine to form thiazolidines or thiazolidine derivatives, such as acetone that reacts with cysteamine to form a different smelling 2,2-dimethyl thiazolidine.

If cysteamine is the reducing agent used in the permanent waving process, it has been found that aromatic aldehydes function best as the reducing agent-reactive compound. Benzaldehyde provides an almond fragrance and functions quite well by itself. A mixture of Benzaldehyde with Methyl Hydrocinnamic acid functions better than either aldehyde alone. Additional examples of aromatic aldehydes for use in the composition and method of the present invention as the reducing agent-reactive compound include o-tolualdehyde; m-tolualdehyde; p-tolualdehyde; salicylaldehyde; p-hydroxybenzaldehyde; anisaldehyde; vanillin; piperonal; phenylacetaldehyde; citronellal; citral; and combinations of any two or more of these aldehydes. A non-aromatic aldehyde that functions well as the reactive compound is cinnamaldehyde. Other aldehydes that may be suitable are 3-Hydroxy propanal; Acetaldehyde; 2-Methyl pentanal; 2-Methyl,3 thio-propanal; 2-Furfural (2-Furancarboxaldehyde); 2-hydroxy ethanal; 5-methyl-2-thiophenecarboxaldehyde; 2-Pyrrolylcarboxaldehyde; 2-Thiocarboxaldehyde; N-Methylpyrrolecarboxaldehyde; 2,2-Dimethyl-1,3-dioxolanecarboxaldehyde; 2-Hydroxy ethanal; Hexanal; Nonanal; Benzaldehyde; Butanal; Phenylacetaldehyde; Heptanal; Propanal; and Undecanal.

Suitable ketones include Acetone; 2,3-Pentanedione; 3-Heptanone; 3,3,-Dimethyl butan-2-one; Hydroxypropanone; Cyclopentanone; Cyclohexanone; 2-Pentanone; 2-Heptanone; 1,3-Dimethoxy acetone; 2,4-Pentanedione; 5-Hydroxy-2-pentanone; 5-methyl-2-thiopenecarboxaldehyde; 2-Octanone; 4-Heptanone; 2-Hexanone; 3-Pentanone; Acetone; Butanone; 3-Hexanone; 2-Undecanone; 2,5-Hexanedione; 3,3-Dimethoxyacetone; and mixtures thereof. Reaction products of these aldehydes with cysteamine, and their fragrance, are disclosed in Dubs, et al. U.S. Pat. No. 3,944,561, directed to thiazolidine flavoring and/or odorant compounds, hereby incorporated by reference. Suitable esters include Ethyl pyruvate; 2-Hydroxyacetic acid, ethyl ester; Dimethyl 1,3-acetonedicarboxylate; Diethyl 1,3-acetonedicarboxylate; Ethyl acetoacetate; Ethyl propanylacetate; and mixtures thereof.

In accordance with a second embodiment of the present invention, instead of using a reactive compound, e.g., carbonyl-containing, to intercept (react with) the reducing agent to prevent or lessen the degree of formation of a reducing agent-hair component reaction product, the above carbonyl-containing compounds can be added to the hair after the reducing agent-hair reaction (and preferably after rinsing the hair) for intercepting (reacting with) a reaction product formed by the reaction of the reducing agent with hair, particularly the cleaved disulfide cystine hair bond itself. The reducing agent reaction product must be intercepted (reacted with a carbonyl-containing reactant) to compete with malodorous products formed as a result of the reaction with the reducing agent used in the permanent wave process.

EXAMPLE 3

A set of hair swatches are pretreated with a composition containing a mixture of Benzaldehyde and Methyl Hydrocinnamic Aldehyde, as detailed in Table I. This is followed by treatment with a permanent wave lotion containing a thiol, e.g., Ammonium Thioglycolate, as the reducing agent. The compounds that form by the reaction of Ammonium Thioglycolate with natural hair aldehydes, without the pretreatment are more odiferous than the compounds that form by the reaction of the Benzaldehyde and Methyl Hydrocinnamic Aldehyde, contained in the pretreatment composition, with Ammonium Thioglycolate.

EXAMPLE 4

Hair swatches are treated with a permanent wave lotion containing Ammonium Thioglycolate as the reducing agent. Hair is rinsed to remove odiferous disulfides formed by the reaction of Ammonium Thioglycolate by thoroughly rinsing the hair, leaving only trace amounts. The rinsed hair then is contacted with the composition of Table I containing about 1% by weight aldehydes to provide the hair with about 0.3 gram aldehydes per 100 grams of hair, uniformly distributed. The hair is then oxidized with hydrogen peroxide in a stoichiometric excess, to assure sufficient $H_2O_2$ for reestablishing the sulfur to sulfur cystine bonds broken by the reducing agent, while reacting a portion of the activated sulfur sites with the aldehyde to reduce the odor of the reconfigured hair.

Optionally, the composition of the present invention includes a conditioner to improve the combing and manageability of the hair. Particularly, suitable conditioners are the polymeric quaternary ammonium salts, such as Polyquaternium 1 through Polyquaternium 14, inclusive, conditioners defined on page 245, CTFA Cosmetic Ingredient Dictionary, Third Edition, 1982, hereby incorporated by reference. The preferred conditioners are Polyquaternium-4, Polyquaternium-10 and Polyquaternium-11. The conditioner, when added, is included in an amount of about 0.01% to about 2.0% by weight of the composition.

Other common cosmetic additives can be incorporated into the permanent wave pretreating compositions of the present invention, as long as the basic properties of hair aldehyde reaction are not substantially adversely affected. These additives include, but are not limited to, commonly used fragrances, dyes, opacifiers, pearlescing agents, thickeners, foam stabilizers, preservatives, water softening agents, acids, bases, buffers and the like; and will usually be present in weight percentages of less than about 1% e.g. about 0.01% to about 1% each, and about 2% to about 5% in total. The composition vehicle is predominantly water.

The composition optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners, such as bentonite. These thickeners, when included, preferably are present in an amount from about 0.1% to about 10% by weight and, in particular, from about 0.5% to about 3% by weight, based on the total weight of the composition.

The composition preferably has the pH in the range of about 2.0 to about 6.0. To achieve the full advantage of the present invention, the composition has a pH of about 3.0 to about 4.0, with best results at a pH in the range of about 3.2 to about 3.5.

Moisturizers optionally are included in the pretreating compositions of the present invention to enhance the curl formation of the permanent wave after application of the pretreating composition of the present invention. The use of polyhydric alcohols or polyhydroxy alkane compounds, such as ethylene glycol, glycerine, propylene glycol, or polyoxyethylene glyceryl ether in this composition leave the hair in better condition for permanent waving due to humectant properties and does not compromise curl formation, but provides the hair with a more uniform and natural curl.

These moisturizers are selected from the group consisting of polyhydroxyalkyl compounds, particularly alkylene glycols and polyalkylene glycols, and especially ethylene glycol and the polyethylene glycols; propylene glycol and the polypropylene glycols; polyethylene glycol glyceryl ethers; ethoxylated fatty alcohols; and fatty alcohol polyglycol ethers. Examples of suitable moisturizers include glycols and triols such as glycerine, ethylene glycol, propylene glycol, 1,3-butylene glycol, 1,2,6-hexanetriol, 1,5-pentanediol, 2-methyl pentanediol-2,4, and 2-ethyl hexanediol-1,3. Further examples of suitable moisturizers include the polyalkylene glycols, such as those compounds having the formula

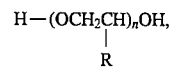

wherein R is H or $CH_3$, and n has an average value of 2 to 600; when R=H, particularly suitable moisturizers have n in the range of 4 to 600; and when R=$CH_3$, particularly suitable moisturizers have n in the range of 2 to 34. The polyalkylene glycols that can be used as moisturizers in the permanent wave composition of the present invention are exemplified by, but not limited to, compounds such as polyethylene glycol 200; polyethylene glycol 400; polyethylene glycol 600; polypropylene glycol 150; tetraethylene glycol; and dipropylene glycol.

Examples of other suitable moisturizers include the polyethylene glycol glyceryl ethers, such as polyethylene glycol 600 glyceryl ether and polyethylene glycol 26 glyceryl ether.

Furthermore, the ethoxylated nonyl phenols and ethoxylated octyl phenols, particularly nonoxynol, $C_9H_{19}C_6H_4(OCH_2CH_2)_n\text{-OH}$, wherein n averages at least 6 and up to about 100; and octoxynol, $C_8H_{17}S_6H_4(OCH_2CH_2)_n\text{-OH}$, wherein n averages at least 7 and up to about 40, also are suitable moisturizers for use in the composition of the present invention. Suitable ethoxylated fatty alcohols for use as moisturizers in the composition of the present invention include compounds having the formula $R\text{-}(OCH_2CH_2)_n OH$, wherein R is an alkyl group containing from about 12 to about 30 carbon atoms and n averages at least 6. In addition, fatty alcohol polyglycol ethers having the formula

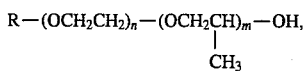

wherein R is an alkyl group containing from about 8 to about 18 carbon atoms, n=0 to 6, m=0 to 6, and n+m is at least 6, also are useful as moisturizers in the composition of the present invention.

The composition of the present invention is easy to use and apply, repeatedly, without damaging the hair while providing a strong, tight curl and leaving the hair soft. The composition can be lotion or water wrapped, sprayed onto the hair, or applied like a shampoo from its container.

Many modifications and variations of the invention as hereinbefore set forth can be made without departing from the spirit and scope thereof and, therefore, only such limitations should be imposed as are indicated by the appended claims.

What is claimed is:

1. A method of reducing malodor resulting from a reaction of a cysteamine reducing agent with hair while permanently waving hair comprising:

contacting the hair with 0.01% to 20%, based on the total weight of hair contacted, of an aldehyde selected from the group consisting of benzaldehyde; methyl hydrocinnamic aldehyde; and mixtures thereof, said aldehyde being more reactive with the cysteamine reducing agent than with natural hair aldehydes, contacting the hair, containing said aldehyde, with the cysteamine reducing agent to break cysteine hair bonds while reacting a portion of the reducing agent with said aldehyde thereby forming a reaction product from the reaction of the cysteamine reducing agent with said aldehyde; and said reaction product having a different odor than a reaction product formed from the reaction of the cysteamine reducing agent with said hair.

2. The method of claim 1, wherein the aldehyde is included in the composition in an amount in the range of about 0.01% to about 10% by weight of the composition.

3. The method of claim 1, wherein the aldehyde included in the composition is substantive to hair upon contact of the hair with the reducing agent.

4. A method of reducing malodor resulting from a reaction of a cysteamine reducing agent with a hair component while permanently waving hair comprising:

contacting the hair with 0.05% to 20% by weight, based on the total weight of hair contacted, of an aldehyde selected from the group consisting of benzaldehyde; methyl hydrocinnamic aldehyde; and mixtures thereof, said aldehyde being more reactive with the cysteamine reducing agent than with natural hair aldehydes; and contacting the hair containing said aldehyde, with the cysteamine reducing agent to break cysteine hair bonds while reacting a portion of the reducing agent with said aldehyde added to the hair, thereby forming a thiazolidine reaction product having a less objectionable odor than thiazolidines formed from a reaction between the cysteamine reducing agent and natural hair aldehydes.

5. A method of reducing malodor in the permanent waving process as a result of a reaction between a cysteamine reducing agent contained in a waving lotion and a reactive hair component comprising:

doping the hair, prior to substantial reaction of the hair with the waving lotion reducing agent, with a fragrant aldehyde reactant selected from the group consisting of benzaldehyde; methyl hydrocinnamic aldehyde; and mixtures thereof, said fragrant aldehyde being more reactive with the cysteamine reducing agent than with natural hair aldehydes, in an amount of 0.01% to 20% fragrant aldehyde, based on the total weight of the hair; and thereafter contacting the hair with the cysteamine reducing agent-containing waving lotion, thereby reacting the cysteamine reducing agent with the fragrant aldehyde reactant and with the hair to permanently wave the hair with less objectionable odor.

6. A method of reducing malodor resulting from a reaction of a cysteamine reducing agent with hair while permanently waving hair comprising:

contacting the hair with 0.01% to 20%, based on the total weight of hair contacted, of a reducing agent-reactive aldehyde selected from the group consisting of benzaldehyde; methyl hydrocinnamic aldehyde; and mixtures thereof, said aldehyde being more reactive with the cysteamine reducing agent than with natural hair aldehydes;

contacting the hair, containing said reactive aldehyde, with the cysteamine reducing agent to break cysteine hair bonds while reacting a portion of the reducing agent with said reactive aldehyde thereby forming a reaction product from the reaction of the cysteamine reducing agent with said reactive aldehyde; and said reaction product having a different odor than a reaction product formed from the reaction of the cysteamine reducing agent with said hair.

7. The method of claim 6, wherein the reactive aldehyde is included in the composition in an amount in the range of about 0.01% to about 10% by weight of the composition.

8. The method of claim 6, wherein the reducing agent-reactive aldehyde is substantive to hair upon contact of the hair with the reducing agent.

9. The method of claim 6, wherein the aldehyde is a mixture of benzaldehyde and methyl hydrocinnamic aldehyde.

* * * * *